United States Patent
Kuga et al.

(10) Patent No.: US 10,420,534 B2
(45) Date of Patent: Sep. 24, 2019

(54) ULTRASONIC DIAGNOSTIC DEVICE, IMAGE PROCESSING DEVICE, AND IMAGE PROCESSING METHOD

(71) Applicant: Toshiba Medical Systems Corporation, Otawara-shi (JP)

(72) Inventors: Itsuki Kuga, Nasushiobara (JP); Magnus Wahrenberg, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 720 days.

(21) Appl. No.: 14/634,177

(22) Filed: Feb. 27, 2015

(65) Prior Publication Data

US 2015/0164475 A1 Jun. 18, 2015

Related U.S. Application Data

(63) Continuation of application No. PCT/JP2013/073445, filed on Aug. 30, 2013.

(30) Foreign Application Priority Data

Aug. 30, 2012 (JP) ................. 2012-190367
Aug. 30, 2013 (JP) ................. 2013-180610

(51) Int. Cl.
*A61B 8/00* (2006.01)
*A61B 8/08* (2006.01)
*G06T 15/08* (2011.01)

(52) U.S. Cl.
CPC .............. *A61B 8/483* (2013.01); *A61B 8/463* (2013.01); *A61B 8/466* (2013.01); *A61B 8/5207* (2013.01);
(Continued)

(58) Field of Classification Search
CPC ......... A61B 8/463; A61B 8/466; A61B 8/483; A61B 8/5207; A61B 8/5238; A61B 8/5246; G06T 15/08
See application file for complete search history.

(56) References Cited

U.S. PATENT DOCUMENTS 6,008,813 A * 12/1999 Lauer ................. G06T 1/60
345/418
6,500,118 B1 12/2002 Hashimoto
(Continued)

FOREIGN PATENT DOCUMENTS

CN 101601593 A 12/2009
CN 101791229 A 8/2010
(Continued)

OTHER PUBLICATIONS

Combined Chinese Office Action and Search Report dated Feb. 1, 2016 in Patent Application No. 201380045448.9 (with English language translation of categories of cited documents).
(Continued)

*Primary Examiner* — Jonathan Cwern
(74) *Attorney, Agent, or Firm* — Oblon, McClelland, Maier & Neustadt, L.L.P.

(57) ABSTRACT

According to one embodiment, an ultrasonic diagnostic device includes a first rendering unit, a second rendering unit, a superimposition processing unit, a display control unit. The first rendering unit generates a first rendering image according to a first rendering method based on volume data collected by three-dimensionally scanning a subject with ultrasonic waves. The second rendering unit generates a second rendering image according to a second rendering method that is different from the first rendering method, based on the volume data. The superimposition processing unit generates a superimposed image in which at least a part of the first rendering image and a part of the (Continued)

second rendering image are superimposed on each other. The display control unit causes a display device to display the superimposed image. The superimposition processing unit adjusts a superimposition ratio of the first and second rendering images in the superimposed image.

12 Claims, 7 Drawing Sheets

(52) U.S. Cl.
CPC ............ *A61B 8/5238* (2013.01); *G06T 15/08* (2013.01); *A61B 8/5246* (2013.01)

(56) References Cited

U.S. PATENT DOCUMENTS

| | | |
|---|---|---|
| 8,988,462 B2 | 3/2015 | Tsujita |
| 9,072,470 B2 | 7/2015 | Sumi et al. |
| 2009/0036749 A1 | 2/2009 | Freiburger et al. |
| 2009/0208080 A1 | 8/2009 | Grau et al. |
| 2009/0306508 A1 | 12/2009 | Yoshida et al. |
| 2011/0245675 A1* | 10/2011 | Yoshida ................ A61B 8/461 600/443 |

FOREIGN PATENT DOCUMENTS

| | | |
|---|---|---|
| JP | 10-146395 A | 6/1998 |
| JP | 2000-132664 A | 5/2000 |
| JP | 2006-130071 A | 5/2006 |
| JP | 2009-501587 A | 1/2009 |
| JP | 2009-034521 A | 2/2009 |
| JP | 2009-078187 A | 4/2009 |
| JP | 2010-188118 A | 9/2010 |
| WO | WO 2011/099410 A1 | 8/2011 |

OTHER PUBLICATIONS

Combined Office Action and Search Report dated Apr. 17, 2017 in Chinese Patent Application No. 201380045448.9 with English translation of category of cited documents).
Office Action dated May 23, 2017 in Japanese Patent Application No. 2013-180610.
International Search Report dated Sep. 24, 2013 for PCT/JP2013/073445 filed on Aug. 30, 2013 with English Translation.
International Written Opinion dated Sep. 24, 2013 for PCT/JP2013/073445 filed on Aug. 30, 2013.
Henrik Wann Jensen, "Global Illumination using Photon Maps", Department of Graphical Communication, The Technical University of Denmark.

* cited by examiner

ULTRASONIC DIAGNOSTIC DEVICE, IMAGE PROCESSING DEVICE, AND IMAGE PROCESSING METHOD

CROSS-REFERENCE TO RELATED APPLICATIONS

This application is a continuation of PCT international application Ser. PCT/JP2013/073445, filed on Aug. 30, 2013 which designates the United States, and which claims the benefit of priority from Japanese Patent Applications No. 2012-190367, filed on Aug. 30, 2012; and No. 2013-180610, filed on Aug. 30, 2013; the entire contents of which are incorporated herein by reference.

FIELD

Embodiments described herein relate generally to an ultrasonic diagnostic device, an image processing device, and an image processing method.

BACKGROUND

In recent years, an ultrasonic diagnostic device that collects volume data by using an ultrasonic probe capable of scanning a subject three-dimensionally has been put to practical use. In such an ultrasonic diagnostic device, rendering is performed with respect to the collected volume data with various kinds of rendering methods. For example, as a rendering method used in the ultrasonic diagnostic device, a volume rendering method of generating a two-dimensional image that reflects three-dimensional information has been known.

In recent years, a rendering method referred to as "global illumination" has been also known. The global illumination is a method of acquiring a more realistic image by rendering volume data, while taking into consideration propagation (such as attenuation or reflection) of light in a real space.

DETAILED DESCRIPTION

Figure 1:
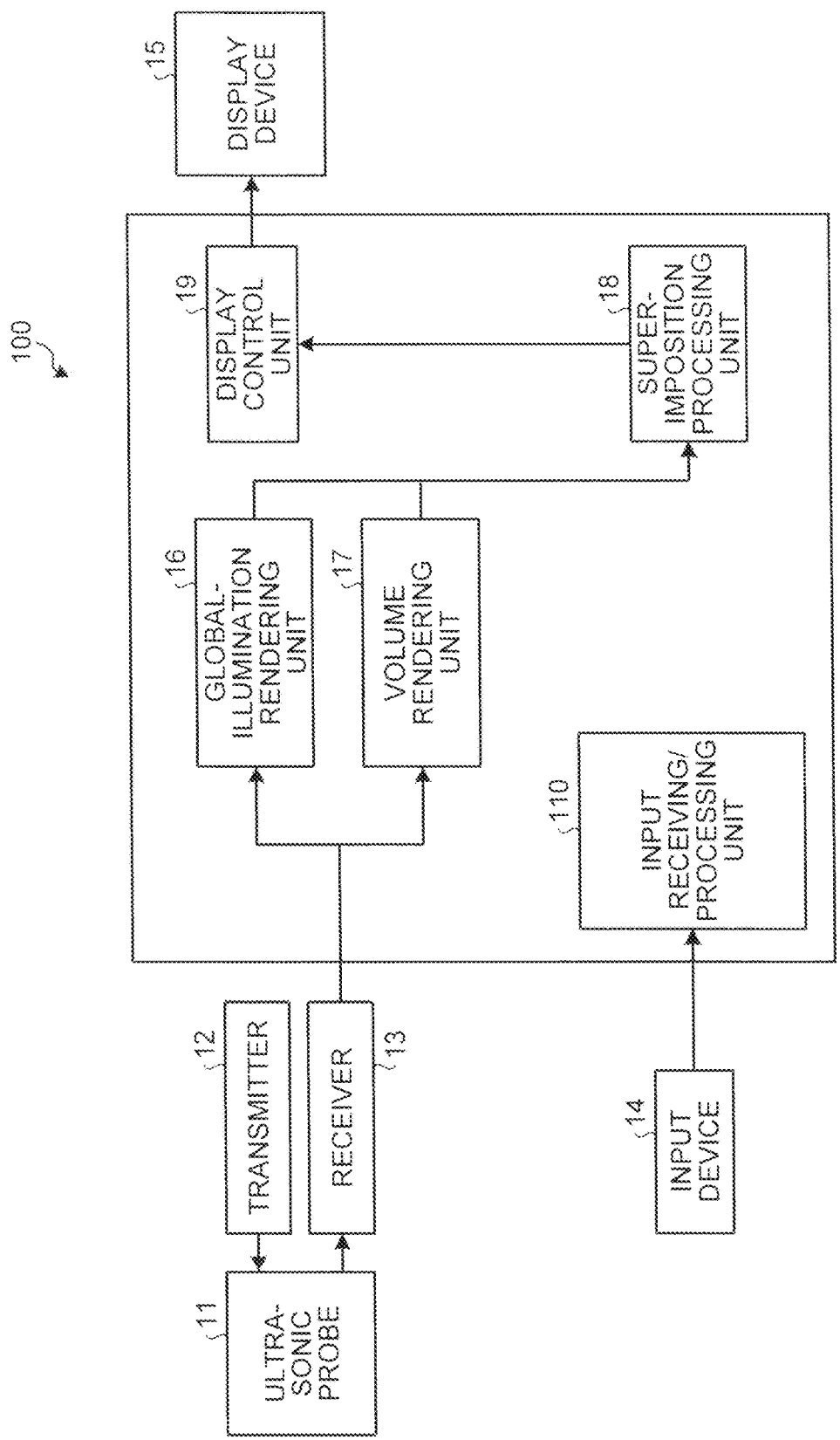
FIG. 1 is a block diagram of a schematic configuration of an ultrasonic diagnostic device according to a first embodiment.

According to one embodiment, an ultrasonic diagnostic device includes a first rendering unit, a second rendering unit, a superimposition processing unit, a display control unit. The first rendering unit generates a first rendering image according to a first rendering method based on volume data collected by three-dimensionally scanning a subject with ultrasonic waves. The second rendering unit generates a second rendering image according to a second rendering method that is different from the first rendering method, based on the volume data. The superimposition processing unit generates a superimposed image in which at least a part of the first rendering image and a part of the second rendering image are superimposed on each other. The display control unit causes a display device to display the superimposed image. The superimposition processing unit adjusts a superimposition ratio of the first and second rendering images in the superimposed image.

Exemplary embodiments of an ultrasonic diagnostic device, an image processing device, and an image processing method are explained below with reference to the accompanying drawings.

First Embodiment

A first embodiment is explained first. An ultrasonic diagnostic device according to the first embodiment generates a global illumination image and a volume rendering image respectively based on volume data collected by three-dimensionally scanning a subject with ultrasonic waves, and displays a superimposed image in which the global illumination image and the volume rendering image are superimposed on each other.

The global illumination image is an image acquired by rendering the volume data by global illumination. In global illumination, voxels are arranged in a three-dimensional space, and a projection image is displayed based on a luminance value allocated to each voxel and a position of an observing point. Brightness of the voxels is changed based on a light source arranged in specific coordinates in the three-dimensional space. Specifically, propagation of light is calculated, assuming that each voxel causes attenuation or scatter reflection of light irradiated from the light source. Therefore, brightness of the voxels on an image changes depending on not only the luminance value allocated to each voxel and the position of the light source but also light attenuated or scatter-reflected by other voxels. For the light source, it can be set from which direction the three-dimensional space is irradiated, how much is the amount of light, and the like. For example, an attenuation coefficient of light when light propagates in the air can be set. When the attenuation coefficient is set, the voxels in an area near the light source are displayed bright, and the voxels far from the light source and the voxels for which light is blocked by other voxels are displayed dark. The light source is not limited to a point light source, and can be parallel light. Brightness of the voxels can be determined, while taking into consideration reflection of light by structures (voxels) or refraction of light, other than the direction of light.

Meanwhile, the volume rendering image is an image acquired by rendering the volume data by volume rendering. In volume rendering, the voxels are arranged in the three-dimensional space, and brightness and color of the respective voxels on the display are set according to a voxel value allocated to each voxel (in the case of volume data in a mode B, according to a luminance value of B). A projection image obtained by projecting the voxels from the observing point is then displayed. A determination of brightness and color of the voxels is performed based on luminance and a parameter such as a color phase specified at the time of rendering. There is no concept of the light source, and the voxels are displayed bright in an area having a high voxel value, even in an area where light is hard to reach or even inside of a lumen.

Conventionally, in global illumination, although a real image can be acquired, the obtained image is different from an image obtained by the conventional volume rendering. Therefore, it is difficult to ascertain which area of the subject an operator is observing, and this causes confusion. Furthermore, according to the setting of the position of the light source, an observation target may be completely in a shade, or the contour of the observation target may become obscure according to how it is shaded, thereby making it difficult to observe a structure by the operator.

On the other hand, according to an ultrasonic diagnostic device 100 of the first embodiment, because the global illumination image and the volume rendering image are superimposed on each other and displayed, the contour of the structure can be supplemented on the global illumination image. Accordingly, even if the position of the light source to be used in global illumination is not appropriately set, the observation target can be observed easily without losing any sight of the structure. The ultrasonic diagnostic device according to the first embodiment is explained below in detail.

FIG. 1 is a block diagram of a schematic configuration of the ultrasonic diagnostic device according to the first embodiment. As shown in FIG. 1, the ultrasonic diagnostic device 100 includes an ultrasonic probe 11, a transmitter 12, a receiver 13, an input device 14, a display device 15, a global-illumination rendering unit 16, a volume rendering unit 17, a superimposition processing unit 18, a display control unit 19, and an input receiving/processing unit 110.

In one embodiment, the ultrasonic diagnostic device 100 includes a processor such as a central processing unit (CPU) or micro processing unit (MPU), and a memory. The memory stores processor-executable instructions that, when executed by the processor, cause the processor to perform processes described later as being performed by one or a plurality of the global-illumination rendering unit 16, the volume rendering unit 17, the superimposition processing unit 18, the display control unit 19, and the input receiving/processing unit 110.

The ultrasonic probe 11 transmits ultrasonic waves to a subject, and receives reflected waves thereof. The ultrasonic probe 11 can collect volume data by three-dimensionally scanning the subject by the ultrasonic waves. The transmitter 12 transmits a drive pulse signal for transmitting the ultrasonic waves to the ultrasonic probe 11. The receiver 13 receives the reflected waves received by the ultrasonic probe 11 as an electric signal. The volume data collected by the ultrasonic probe 11 is transmitted to the global-illumination rendering unit 16 and the volume rendering unit 17 described later via the receiver 13.

The input device 14 receives various operations from an operator. For example, the input device 14 is a mouse, a keyboard, a button, a panel switch, a touch command screen, a foot switch, a trackball, or the like. The display device 15 displays various images, GUI (Graphical User Interface) for receiving an input of various operations from the operator, and the like. For example, the display device 15 is a liquid crystal monitor, a CRT (Cathode Ray Tube) monitor, or the like.

The global-illumination rendering unit 16 renders the volume data collected by the ultrasonic probe 11 by global illumination to generate a global illumination image.

Specifically, when the volume data is transmitted from the receiver 13, the global-illumination rendering unit 16 renders the transmitted volume data by global illumination to generate a global illumination image. The global-illumination rendering unit 16 transmits the generated global illumination image to the superimposition processing unit 18 described later.

For example, the global-illumination rendering unit 16 generates a global illumination image according to a method using photon mapping explained below (for example, see Henrik Wann Jensen, "Global Illumination using Photon Maps" Department of Graphical Communication, The Technical University of Denmark).

In this method, photon is a definition for an algorism that discretizes light for expressing the light on a computer and conveys optical energy per unit time. In this method, collisions of preset number of photons in a system or set number of photons by an operator are calculated in a target volume and are arranged in a scene.

Various parameters (various attributes expressing propagation of light) can be set to the photons. However, it is assumed here that only attenuation (absorption by an object) is calculated for simplifying calculation. An absorptivity indicating which component is to be attenuated how much, of RGB components included in the photon, is set in an object (a voxel). Attenuation of photons occurs depending on the absorptivity for each of the RGB components set in the object. The absorptivity is set beforehand in the system or set by the operator. The behavior of the photon at a certain point is calculated based on the probability theory and recorded (mapped), thereby completing a photon map, which is three-dimensional data.

After completion of the photon map, a rendering process is performed. The rendering process is performed by a ray-tracing method. At the time of looking up the volume data in calculation, the distribution density of photons around a corresponding (x, y, z) position is used to set the brightness according to the density. At this time, a threshold and a degree of transparency can be set in the same method as in normal volume rendering. Accordingly, the global illumination image is generated.

The volume rendering unit 17 renders the volume data collected by the ultrasonic probe 11 by volume rendering to generate a volume rendering image.

Specifically, when the volume data is transmitted from the receiver 13, the volume rendering unit 17 renders the transmitted volume data by volume rendering to generate a volume rendering image. The volume rendering unit 17 transmits the generated volume rendering image to the superimposition processing unit 18 described later.

For example, the volume rendering unit 17 renders the volume data by using the ray-tracing method to generate the volume rendering image.

The superimposition processing unit 18 generates a superimposed image in which a global illumination image generated by the global-illumination rendering unit 16 and a volume rendering image generated by the volume rendering unit 17 are superimposed on each other.

Specifically, when the global illumination image is transmitted from the global-illumination rendering unit 16 and the volume rendering image is transmitted from the volume rendering unit 17, the superimposition processing unit 18 generates a superimposed image in which the global illumination image and the volume rendering image are superimposed on each other. The superimposition processing unit 18 then transmits the generated superimposed image to the display control unit 19 described later.

For example, as shown in Equations (1) to (3) mentioned below, the superimposition processing unit 18 combines a global illumination image and a volume rendering image at a superimposition ratio set by an operator by linear interpolation for each of the RGB components, thereby generating a superimposed image.

$$OutputImge\_r=(Igi\_r*(1-ratio))+(Ivr\_r*ratio) \quad (1)$$

$$OutputImge\_g=(Igi\_g*(1-ratio))+(Ivr\_g*ratio) \quad (2)$$

$$OutputImge\_b=(Igi\_b*(1-ratio))+(Ivr\_b*ratio) \quad (3)$$

In the Equations (1) to (3) mentioned above, OutputImage denotes a superimposed image, Igi denotes a global illumination image, and Ivr denotes a volume rendering image. Each "_r" respectively added to OutputImage, Igi, and Ivr denotes an R (Red) component, "_g" denotes a G (Green) component, and "_b" denotes a B (Blue) component. In addition, "ratio" denotes the superimposition ratio set by the operator.

The superimposition processing unit 18 superimposes a two-dimensional image generated as a result of rendering by the global-illumination rendering unit 16 and a two-dimensional image generated as a result of rendering by the volume rendering unit 17 on each other to generate a superimposed image. Alternatively, the superimposition processing unit 18 can generate a superimposed image by superimposing three-dimensional data generated before rendering is performed by the global-illumination rendering unit 16 and three-dimensional data generated before rendering is performed by the volume rendering unit 17 on each other.

The display control unit 19 causes the display device 15 to display the superimposed image generated by the superimposition processing unit 18. Specifically, when the superimposed image is transmitted from the superimposition processing unit 18, the display control unit 19 causes the display device 15 to display the transmitted superimposed image.

The input receiving/processing unit 110 receives various operations via the input device 14, and inputs a command corresponding to the received operation to the respective units of the ultrasonic diagnostic device 100. In FIG. 1, arrows between the input receiving/processing unit 110 and respective units are omitted.

For example, the input receiving/processing unit 110 receives an operation to set rendering conditions associated with global illumination and rendering conditions associated with volume rendering. The rendering conditions associated with global illumination includes the position of the observing point, a projection direction of the volume data, the position of the light source, an amount of light of the light source, an irradiation direction of the light source, and the like. The rendering conditions associated with volume rendering includes the position of the observing point, the projection direction of the volume data, brightness and color on the display of the voxel corresponding to the voxel value, and the like. However, common conditions are used between global illumination and volume rendering regarding the conditions of the position of the observing point and the projection direction of the volume data. Upon reception of the rendering conditions associated with global illumination, the input receiving/processing unit 110 transmits the received rendering conditions to the global-illumination rendering unit 16. Upon reception of the rendering conditions associated with volume rendering, the input receiving/processing unit 110 also transmits the received rendering conditions to the volume rendering unit 17. The global-illumination rendering unit 16 and the volume rendering unit 17 having received the rendering conditions respectively render the volume data based on the transmitted rendering conditions.

Furthermore, for example, the input receiving/processing unit 110 receives an operation to rotate or shift the superimposed image displayed on the display device 15. Upon reception of the operation, the input receiving/processing unit 110 transmits a command to rotate or shift the global illumination image to the global-illumination rendering unit 16, and transmits a command to rotate or shift the volume rendering image to the volume rendering unit 17. At this time, a rotation amount and a shift amount are common to the global illumination image and the volume rendering image. The global-illumination rendering unit 16 having received the command generates a rotated or shifted global illumination image by re-rendering, and transmits the generated global illumination image to the superimposition processing unit 18. Meanwhile, upon reception of the command from the input receiving/processing unit 110, the volume rendering unit 17 generates a rotated or shifted volume rendering image by re-rendering, and transmits the generated volume rendering image to the superimposition processing unit 18. The superimposition processing unit 18 generates a superimposed image in which the transmitted global illumination image and volume rendering image are superimposed on each other, and transmits the generated superimposed image to the display control unit 19. Accordingly, the rotated or shifted superimposed image is displayed on the display device 15.

Further, for example, the input receiving/processing unit 110 receives an operation to change the superimposition ratio between the global illumination image and the volume rendering image in the superimposed image displayed on the display device 15. The superimposition processing unit 18 adjusts the superimposition ratio between the global illumination image and the volume rendering image in the superimposed image according to the operation received by the input receiving/processing unit 110.

As a specific example, for example, upon reception of an operation to set the superimposition ratio of the volume rendering image to zero, the input receiving/processing unit 110 transmits a command to set the superimposition ratio of the volume rendering image in the superimposed image to zero to the superimposition processing unit 18. The superimposition processing unit 18 having received the command skips the process to generate the superimposed image, and transmits only the global illumination image to the display control unit 19. Accordingly, only the global illumination image is displayed on the display device 15.

Further, upon reception of an operation to change the superimposition ratio of the volume rendering image, the input receiving/processing unit 110 transmits to the superimposition processing unit 18 a command to change the superimposition ratio of the volume rendering image to the received superimposition ratio. The superimposition processing unit 18 having received the command changes the superimposition ratio of the volume rendering image, and regenerates a superimposed image. The superimposition processing unit 18 transmits the generated superimposed image to the display control unit 19. Accordingly, the superimposed image in which the volume rendering image is superimposed on the global illumination image with the changed superimposition ratio is displayed on the display device 15. When the superimposition ratio is changed in this manner, only the superimposed image can be regenerated. Therefore, when two-dimensional images after rendering are superimposed on each other, re-rendering does not need to be performed by the global-illumination rendering unit 16 and the volume rendering unit 17.

The superimposition processing unit 18 regenerates a superimposed image and transmits the superimposed image to the display control unit 19, every time the superimposition ratio of the volume rendering image is changed by an operator. Accordingly, while gradually changing the superimposition ratio of the volume rendering image, the operator can observe the change in the superimposed image on a real-time basis. As a result, the operator can easily recognize positional correspondence between the global illumination image and the volume rendering image.

Furthermore, by adjusting the position of the light source for global illumination, the global illumination image may become too bright or too dark as a whole. For example, when lots of voxels having a low attenuation coefficient are arranged at a position very close to the position of the light source and the observing point, or the amount of light of the light source is set very large, the global illumination image becomes too bright. On the other hand, when the position of the light source is set to an opposite side of the voxel with respect to the observing point, or the amount of light of the light source is set very small, the global illumination becomes too dark. When the superimposed image displayed on the display device 15 is too bright or too dark as a whole during adjustment of the light source, the operator can increase the superimposition ratio of the volume rendering image, thereby making the contour of the observation target easily visible. Further, as a result of adjustment of the position of the light source, when the global illumination image is displayed clearly and superimposition of the volume rendering image is not required, the operator can decrease the superimposition ratio of the volume rendering image, thereby enabling to observe only the global illumination image.

Figure 2:
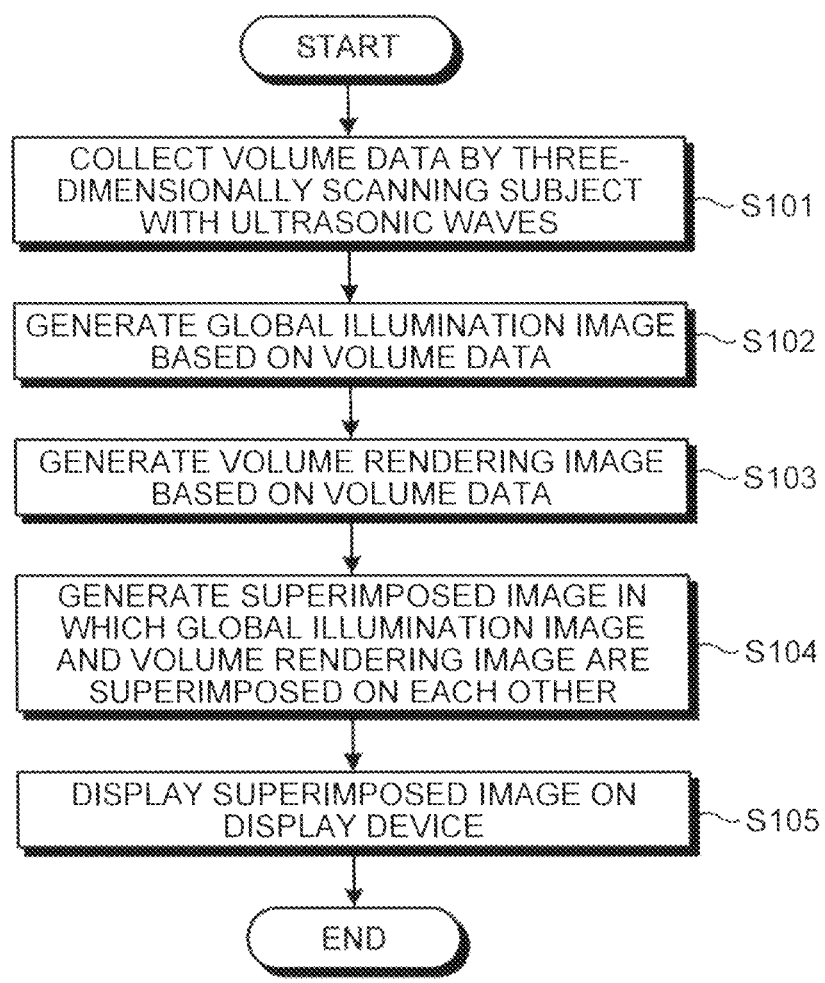
FIG. 2 is a flowchart of a process procedure of a process performed by the ultrasonic diagnostic device according to the first embodiment.

A process performed by the ultrasonic diagnostic device 100 according to the first embodiment is explained next in detail. FIG. 2 is a flowchart of a process procedure of a process performed by the ultrasonic diagnostic device according to the first embodiment. The process procedure from collection of volume data to display of the superimposed image by the ultrasonic diagnostic device 100 is explained here.

As shown in FIG. 2, in the ultrasonic diagnostic device 100, the ultrasonic probe 11 first scans a subject three-dimensionally with ultrasonic waves so as to include an observation target to collect volume data (Step S101).

Subsequently, the global-illumination rendering unit 16 generates a global illumination image based on the collected volume data (Step S102). The volume rendering unit 17 also generates a volume rendering image based on the collected volume data (Step S103).

Thereafter, the superimposition processing unit 18 generates a superimposed image in which the global illumination image generated by the global-illumination rendering unit 16 and the volume rendering image generated by the volume rendering unit 17 are superimposed on each other (Step S104). The display control unit 19 causes the display device 15 to display the superimposed image generated by the superimposition processing unit 18 (Step S105).

In the process procedure described above, generation of a global illumination image by the global-illumination rendering unit 16 and generation of a volume rendering image by the volume rendering unit 17 can be performed in parallel, or after generation of one of the images is complete, generation of the other can be performed.

As described above, according to the first embodiment, because the global illumination image and the volume rendering image are superimposed on each other and displayed, the contour of a structure is supplemented on the global illumination image, and as a result, an operator can easily observe the observation target on the global illumination image. Furthermore, according to the first embodiment, the operator can visually comprehend the correspondence between the respective images in a stepwise manner, by observing the observation target while changing the superimposition ratio between the volume rendering image and the global illumination image.

In the first embodiment, there has been explained an example in which the global-illumination rendering unit 16 and the volume rendering unit 17 generate rendering images (a global illumination image and a volume rendering image) by using volume data received from the receiver 13. However, the global-illumination rendering unit 16 and the volume rendering unit 17 can generate a rendering image by using volume data stored in a storage unit provided in the ultrasonic diagnostic device 100.

In the first embodiment, there has been explained an example in which the global-illumination rendering unit 16 generates a global illumination image according to a method using the photon mapping. However, the global-illumination rendering unit 16 can generate a global illumination image according to another type of algorism. For example, the global-illumination rendering unit 16 can generate an image corresponding to a global illumination image by using various methods such as a radiosity method, specular mapping, or surface rendering.

In the first embodiment, there has been explained an example in which the global-illumination rendering unit 16 adds only attenuation at the time of generating a global illumination image. However, the global-illumination rendering unit 16 can generate a global illumination image by adding another effect of a light source. For example, the global-illumination rendering unit 16 can add reflection, scattering, or the like to generate a global illumination image.

In the first embodiment, there has been explained an example in which the superimposition processing unit 18 generates a superimposed image by linear interpolation. However, the superimposition processing unit 18 can generate a superimposed image according to another type of algorism. For example, the superimposition processing unit 18 compares the strength of the global illumination image with the strength of the volume rendering image at a certain point weighted based on the superimposition ratio, and can adopt an image having a low strength or an image having a high strength to generate the superimposed image. The contour of the structure can be acquired even by this algorism.

In the first embodiment, there has been explained an example in which the display device 15 displays only a global illumination image when the superimposition processing unit 18 sets the superimposition ratio of a volume rendering image to zero. However, when the superimposition processing unit 18 sets the superimposition ratio to zero, the display device 15 can display only a volume rendering image. That is, the superimposition ratio can be the superimposition ratio of the volume rendering image with respect to a global illumination image, or can be the superimposition ratio of a global illumination image with respect to a volume rendering image.

(Second Embodiment)

A second embodiment is explained next. The first embodiment has explained an example in which an operator changes a superimposition ratio. In the second embodiment, an example in which the superimposition ratio is automatically adjusted by an ultrasonic diagnostic device is explained.

Figure 3:
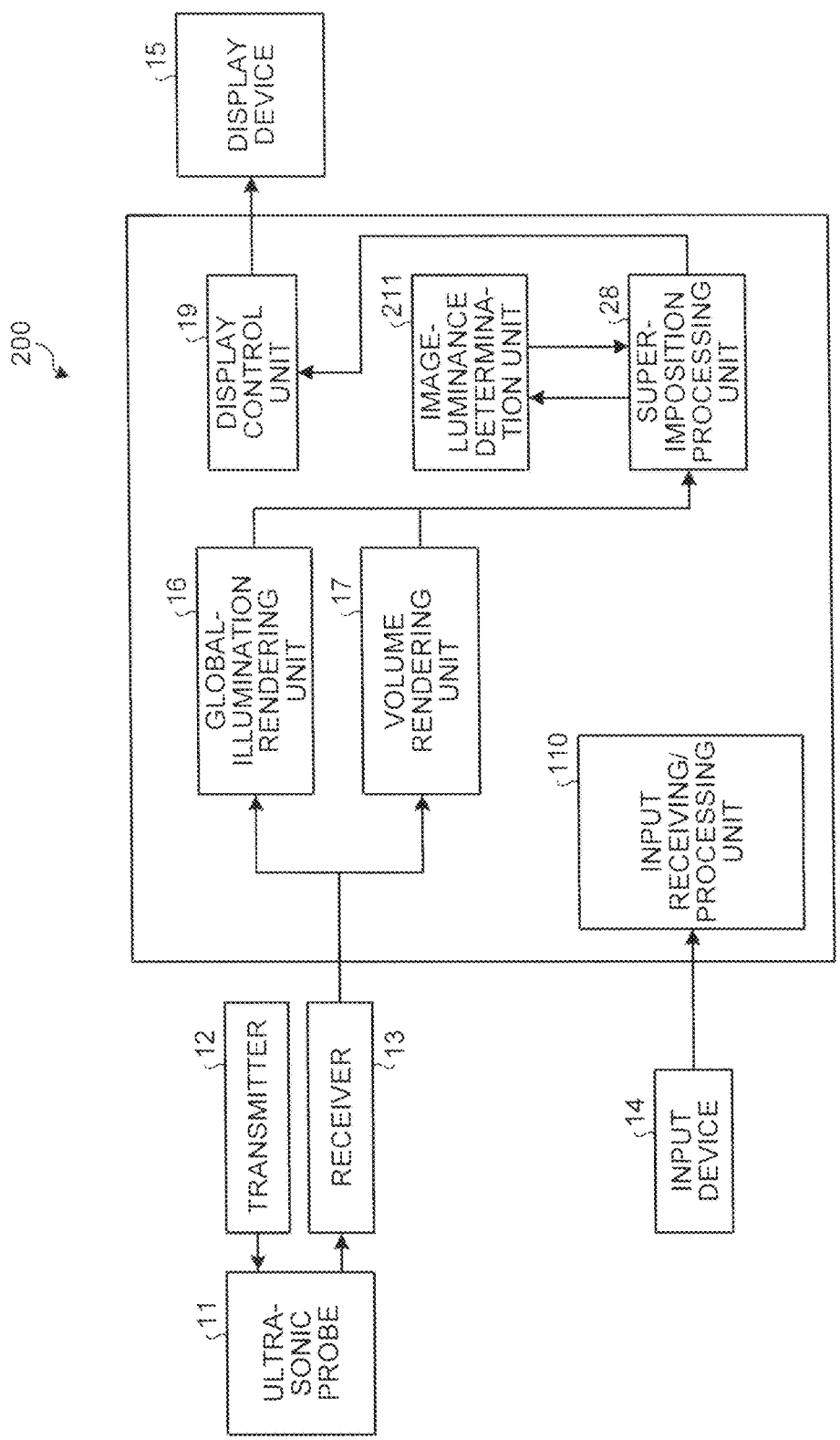
FIG. 3 is a block diagram of a schematic configuration of an ultrasonic diagnostic device according to a second embodiment.

FIG. 3 is a block diagram of a schematic configuration of an ultrasonic diagnostic device according to the second embodiment. As shown in FIG. 3, an ultrasonic diagnostic device 200 according to the second embodiment includes the ultrasonic probe 11, the transmitter 12, the receiver 13, the input device 14, the display device 15, the global-illumination rendering unit 16, the volume rendering unit 17, a superimposition processing unit 28, the display control unit 19, the input receiving/processing unit 110, and an image-luminance determination unit 211.

In the following descriptions, elements having functions identical to those of respective elements shown in FIG. 1 are denoted by like reference signs, and detailed explanations thereof will be omitted. In the second embodiment, the superimposition processing unit 28 and the image-luminance determination unit 211 are different from the first embodiment. In the ultrasonic diagnostic device 200 according to the second embodiment, a process procedure from collection of volume data to display of the superimposed image is the same as that shown in FIG. 2.

The superimposition processing unit 28 generates a superimposed image in which a global illumination image generated by the global-illumination rendering unit 16 and a volume rendering image generated by the volume rendering unit 17 are superimposed on each other.

Specifically, when the global illumination image is transmitted from the global-illumination rendering unit 16 and the volume rendering image is transmitted from the volume rendering unit 17, the superimposition processing unit 28 generates a superimposed image in which the global illumination image and the volume rendering image are superimposed on each other. The superimposition processing unit 28 then transmits the generated superimposed image to the display control unit 19 and the image-luminance determination unit 211 described later.

For example, as shown in Equations (1) to (3) mentioned below, the superimposition processing unit 28 combines a global illumination image and a volume rendering image at a superimposition ratio set in the system as an initial value by linear interpolation for each of the RGB components, thereby generating a superimposed image.

$$OutputImge\_r = (Igi\_r*(1-ratio)) + (Ivr\_r*ratio) \quad (1)$$

$$OutputImge\_g = (Igi\_g*(1-ratio)) + (Ivr\_g*ratio) \quad (2)$$

$$OutputImge\_b = (Igi\_b*(1-ratio)) + (Ivr\_b*ratio) \quad (3)$$

In the Equations (1) to (3) mentioned above, OutputImage denotes a superimposed image, Igi denotes a global illumination image, and Ivr denotes a volume rendering image. Each "_r" respectively added to OutputImage, Igi, and Ivr denotes an R (Red) component, "_g" denotes a G (Green) component, and "_b" denotes a B (Blue) component. In addition, "ratio" denotes the superimposition ratio set in the system.

The superimposition processing unit 28 superimposes a two-dimensional image generated as a result of rendering by the global-illumination rendering unit 16 and a two-dimensional image generated as a result of rendering by the volume rendering unit 17 on each other to generate a superimposed image. Alternatively, the superimposition processing unit 28 can generate the superimposed image by superimposing three-dimensional data generated before rendering is performed by the global-illumination rendering unit 16 and three-dimensional data generated before rendering is performed by the volume rendering unit 17 on each other.

The image-luminance determination unit 211 determines whether the superimposed image is suitable for observation based on a luminance value of the superimposed image displayed on the display device 15.

Specifically, when the superimposed image is transmitted from the superimposition processing unit 28, the image-luminance determination unit 211 statistically analyzes the luminance value of the transmitted superimposed image to determine whether the superimposed image is suitable for observation. When determining that the superimposed image is not suitable for observation, the image-luminance determination unit 211 transmits a command to regenerate a superimposed image by increasing the superimposition ratio of the volume rendering image to the superimposition processing unit 28. Upon reception of the command, the superimposition processing unit 28 increases the superimposition ratio of the volume rendering image only by a predetermined value to regenerate a superimposed image. The superimposition processing unit 28 then transmits the generated superimposed image to the display control unit 19. Consequently, the superimposed image in which the superimposition ratio of the volume rendering image is increased is displayed on the display device 15. When determining that the superimposed image is suitable for observation, the image-luminance determination unit 211 does not transmit the command to the superimposition processing unit 28.

For example, when the superimposed image is transmitted from the superimposition processing unit 28, the image-luminance determination unit 211 generates a luminance histogram of the transmitted superimposed image. The image-luminance determination unit 211 analyzes the generated histogram, and when the histogram is statistically biased to an extremely low luminance value (too dark) or an extremely high luminance value (too bright), the image-luminance determination unit 211 determines that the superimposed image as an analysis target is not suitable for observation. At this time, for example, the image-luminance determination unit 211 calculates a mean luminance value or a variance value of the entire superimposed image. When the calculated mean luminance value is lower than a predetermined lower limit threshold or higher than a predetermined higher limit threshold, or the variance value is smaller than a predetermined threshold, the image-luminance determination unit 211 determines that the superimposed image is not suitable for observation. When the histogram is statistically biased to either the extremely low luminance value or the extremely high luminance value, in either case, it means that the contour of a structure becomes faded on the global illumination image in the superimposed image. In such a case, a superimposed image in which the superimposition ratio of the volume rendering image is increased by the superimposition processing unit 28 is automatically displayed on the display device 15.

The image-luminance determination unit 211 can repeatedly perform a determination of the superimposed image and change of the superimposition ratio by a predetermined number of times. Furthermore, the image-luminance determination unit 211 can receive an operation to set or change the threshold via the input device 14 and the input receiving/ processing unit 110 and perform the determination of the superimposed image by using the received threshold.

The image-luminance determination unit 211 can perform the analysis of the histogram by using the whole luminance value in the superimposed image or by using a half luminance value in the superimposed image or a luminance value in an arbitrary area set in a central part of the superimposed image. The image-luminance determination unit 211 can perform an initial determination by using a luminance value of the global illumination image used in the superimposed image as a determination target, not by using the luminance value of the superimposed image.

The image-luminance determination unit 211 monitors a positional relation among the observing point used for global illumination and volume rendering, the light source used for global illumination, and the structure included in the volume data, and when the light source moves behind the structure, the image-luminance determination unit 211 can determine that the superimposed image is not suitable for observation.

When increasing the superimposition ratio of the volume rendering image, the superimposition processing unit 28 can notify an operator that the superimposition ratio of the volume rendering image has been increased. For example, the superimposition processing unit 28 causes the display unit 15 to display a numerical value or a diagram indicating the superimposition ratio of the volume rendering image via the display control unit 19.

When increasing the superimposition ratio of the volume rendering image, the superimposition processing unit 28 can display a global illumination image and a volume rendering image, respectively generated as a single image, in parallel with a superimposed image. With this arrangement, when setting of the light source is not appropriate, the operator can ascertain the position of the light source by comparing the global illumination image and the volume rendering image, respectively generated as a single image, with each other.

As described above, according to the second embodiment, because the superimposition ratio is automatically adjusted by the ultrasonic diagnostic device, the contour information of the structure is supplemented with respect to the global illumination image at all times, and as a result, the operator can easily observe the observation target on the global illumination image. Further, it can be reliably prevented that the operator loses sight of the observation target.

Figure 4:
FIG. 4 is an example of a global illumination image generated by a global-illumination rendering unit according to the first or second embodiment.
Figure 5:
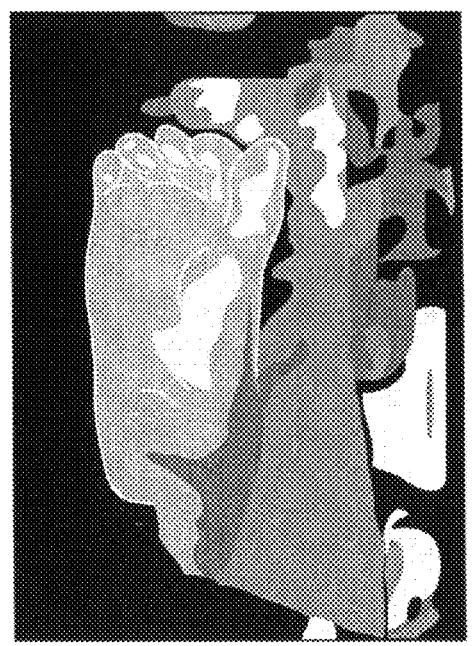
FIG. 5 is an example of a volume rendering image generated by a volume rendering unit according to the first or second embodiment.
Figure 6:
FIG. 6 is an example of a superimposed image generated by a superimposition processing unit according to the first or second embodiment.

Effects achieved by the ultrasonic diagnostic device according to the first and second embodiments are explained specifically with reference to FIGS. 4 to 6. FIG. 4 is an example of a global illumination image generated by the global-illumination rendering unit according to the first or second embodiment. FIG. 5 is an example of a volume rendering image generated by the volume rendering unit according to the first or second embodiment. FIG. 6 is an example of a superimposed image generated by the superimposition processing unit according to the first or second embodiment. FIGS. 4 to 6 depict images of a foot of the same pre-born child, and conceptually depict each rendering image.

As shown in FIG. 4, there is a sense of depth because the global illumination image is shaded. However, the contour of the structure, for example, toes cannot be clearly drawn. On the other hand, as shown in FIG. 5, in the volume rendering image, although the contour of the structure is clear, the image lacks a sense of depth because it is not shaded.

On the other hand, in the superimposed image in which the global illumination image and the volume rendering image are superimposed on each other, there is a sense of depth because of a shadow cast by global illumination, and the contour information of the structure is supplemented by the volume rendering image. As a result, toes can be seen separately from each other. In this manner, in the superimposed image generated by the superimposition processing unit, by superimposing the volume rendering image, the contour of the structure can be supplemented in the global illumination image, if not completely shaded. That is, because the global illumination image and the volume rendering image supplement each other, a favorable rendering image can be acquired.

In the above embodiments, a case where the superimposition ratio is changed by an operator and a case where the ultrasonic diagnostic device automatically adjusts the superimposition ratio have been explained separately. However, the ultrasonic diagnostic device can have the configuration explained in the first embodiment and the configuration explained in the second embodiment. In this case, for example, even if an operator sets the superimposition ratio of the volume rendering image, when it is detected that the luminance is biased in the superimposed image, the ultrasonic diagnostic device automatically adjusts the superimposition ratio.

In the above embodiments, there has been explained a case where the ultrasonic diagnostic device processes volume data. However, the processing with respect to the volume data can be performed by an image processing device independently installed from the ultrasonic diagnostic device. In this case, the image processing device includes an acquisition unit, a first rendering unit, a second rendering unit, a superimposition processing unit, and a display control unit.

The acquisition unit acquires volume data obtained by three-dimensionally scanning a subject with ultrasonic waves. For example, the acquisition unit acquires the volume data by receiving the volume data from a database of an ultrasonic diagnostic device or a PACS (Picture Archiving and Communication Systems) or a database of an electronic medical record system. The first rendering unit generates a global illumination image based on the volume data acquired by the acquisition unit. The second rendering unit generates a volume rendering image based on the volume data acquired by the acquisition unit. The superimposition processing unit generates a superimposed image in which the global illumination image generated by the first rendering unit and the volume rendering image generated by the second rendering unit are superimposed on each other. The display control unit causes a display device to display the superimposed image generated by the superimposition processing unit.

The image processing method explained in the above embodiments can be realized by executing an image processing program prepared beforehand by a computer such as a personal computer or a workstation. In this case, the image processing program causes the computer to execute an acquiring procedure, a first rendering procedure, a second rendering procedure, a superimposition processing procedure, and a display control procedure.

In the acquiring procedure, the computer acquires the volume data obtained by three-dimensionally scanning a subject with ultrasonic waves. For example, the computer acquires the volume data received from a database of the ultrasonic diagnostic device or the PACS (Picture Archiving and Communication Systems) or a database of the electronic medical record system. In the first rendering procedure, the computer generates a global illumination image based on the volume data acquired by the acquiring procedure. In the second rendering procedure, the computer generates a volume rendering image based on the volume data acquired by the acquiring procedure. In the superimposition processing procedure, the computer generates a superimposed image in which the global illumination image generated by the first rendering procedure and the volume rendering image generated by the second rendering procedure are superimposed on each other. In the display control procedure, the computer causes the display device to display the superimposed image generated by the superimposition processing procedure.

The image processing program mentioned above can be distributed via a network such as the Internet. Furthermore, the image processing program can be executed by recording it in a computer readable recording medium such as a hard disk, a flexible disk (FD), a CD-ROM (Compact Disk Read Only Memory), an MO (Magneto-Optical disk), and a DVD (Digital Versatile Disk) and reading it from the recording medium by a computer.

The respective embodiments described above can be modified as follows.

For example, in the second embodiment described above, there has been explained an example in which the superimposition processing unit 28 adjusts the superimposition ratio of a rendering image based on a superimposed image. However, the superimposition processing unit 28 can adjust the superimposition ratio based on a global illumination image. In this case, for example, the image-luminance determination unit 211 uses a global illumination image generated by the global-illumination rendering unit 16 instead of a superimposed image generated by the superimposition processing unit 28 to determine whether the global illumination image is suitable for observation, according to the determination method based on the luminance value explained in the second embodiment.

The superimposition processing unit can superimpose at least a part of the global illumination image and a part of the volume rendering image on each other. In this case, for example, the superimposition processing unit superimposes the global illumination image and the volume rendering image for a predetermined area of the superimposed image.

For example, the superimposition processing unit superimposes the global illumination image and the volume rendering image in an area specified by an operator. Specifically, the superimposition processing unit receives an operation to set an area of interest on the global illumination image or on the superimposed image via the input device 14 and the input receiving/processing unit 110. The number of areas of interest received by the superimposition processing unit from the operator can be one or plural. The superimposition processing unit then superimposes the global illumination image and the volume rendering image for the area of interest set by the operator. Accordingly, the operator can arbitrarily specify an area in which the operator wishes to highlight the contour of the structure on the global illumination image or on the superimposed image.

For example, the superimposition processing unit superimposes the global illumination image and the volume rendering image in an area, which is darker or brighter than a predetermined reference on the global illumination image or on the superimposed image. Specifically, the superimposition processing unit extracts an area formed of pixels whose luminance values are lower than a predetermined threshold on the global illumination image or on the superimposed image and superimposes the global illumination image and the volume rendering image on each other in the extracted area. Accordingly, the superimposition processing unit can automatically highlight the contour of the structure in an area, which is shadowed and becomes invisible. Alternatively, the superimposition processing unit extracts an area formed of pixels whose luminance values are equal to or higher than the predetermined threshold on the global illumination image or on the superimposed image and superimposes the global illumination image and the volume rendering image on each other in the extracted area. Accordingly, the superimposition processing unit can automatically highlight the contour of the structure in an area, which is too bright and hardly visible.

When superimposing the global illumination image and the volume rendering image on each other only in the predetermined area as described above, the superimposition processing unit performs the superimposition processing such that the volume rendering image is superimposed locally only on a predetermined area in the global illumination image. Alternatively, the superimposition processing unit sets the superimposition ratio of the volume rendering image to be larger than zero in a predetermined area, and sets the superimposition ratio to zero in other areas to perform the superimposition processing. As a result, the superimposition processing unit can superimpose the respective rendering images on each other only in the predetermined area.

For example, the superimposition processing unit can divide the superimposed image into a plurality of sections, and set the superimposition ratio for each of the sections. In this case, for example, the superimposition processing unit divides the superimposed image into a predetermined number of sections having a predetermined shape. Alternatively, the superimposition processing unit can divide the superimposed image into sections having a predetermined size and shape.

Figure 7:
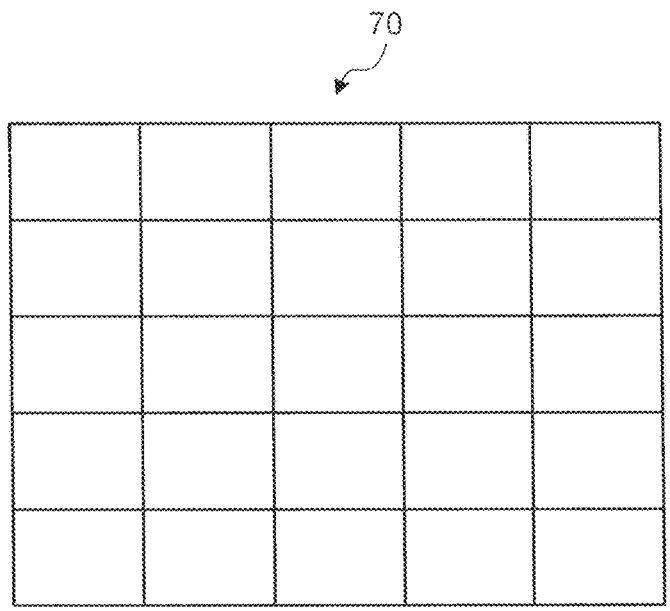
FIG. 7 is an explanatory diagram of an example of divisions of a superimposed image by a superimposition processing unit.

FIG. 7 is an explanatory diagram of an example of divisions of a superimposed image by the superimposition processing unit. For example, as shown in FIG. 7, the superimposition processing unit divides a superimposed image 70 into square sections in a matrix of five rows and five columns. For example, the superimposition processing unit then calculates a mean value of pixel values included in the section of the global illumination image for each of the divided sections, and sets the superimposition ratio of the volume rendering image in each of the sections according to the calculated mean value. At this time, for example, the superimposition processing unit sets the superimposition ratio of the volume rendering image for each of the sections, based on a relation between a predetermined luminance value of the global illumination image and the superimposition ratio of the volume rendering image.

Figure 8:
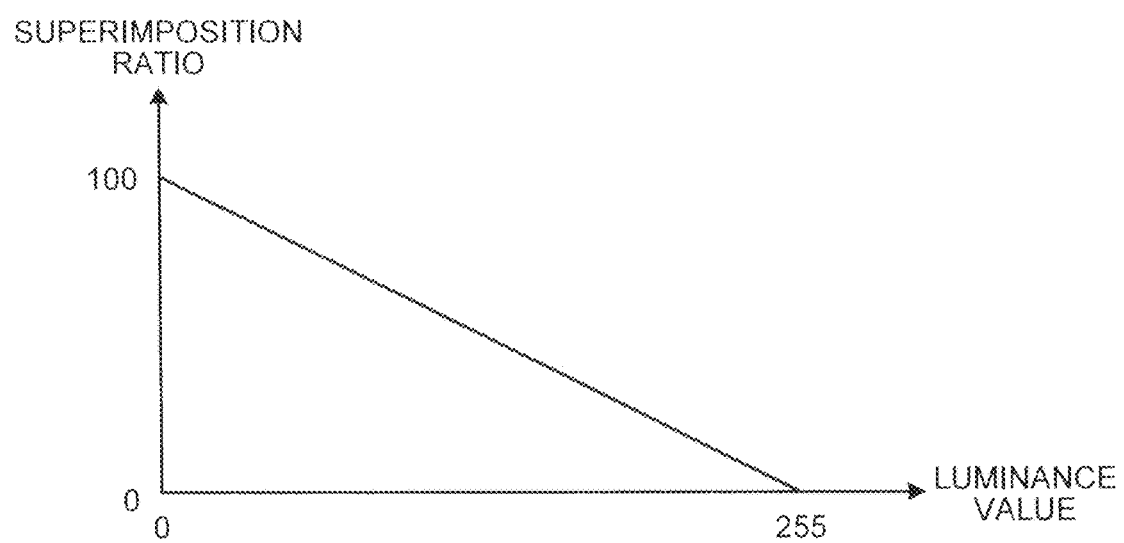
FIGS. 8 to 10 are explanatory diagrams of examples in which the superimposition processing unit sets a superimposition ratio.
Figure 9:
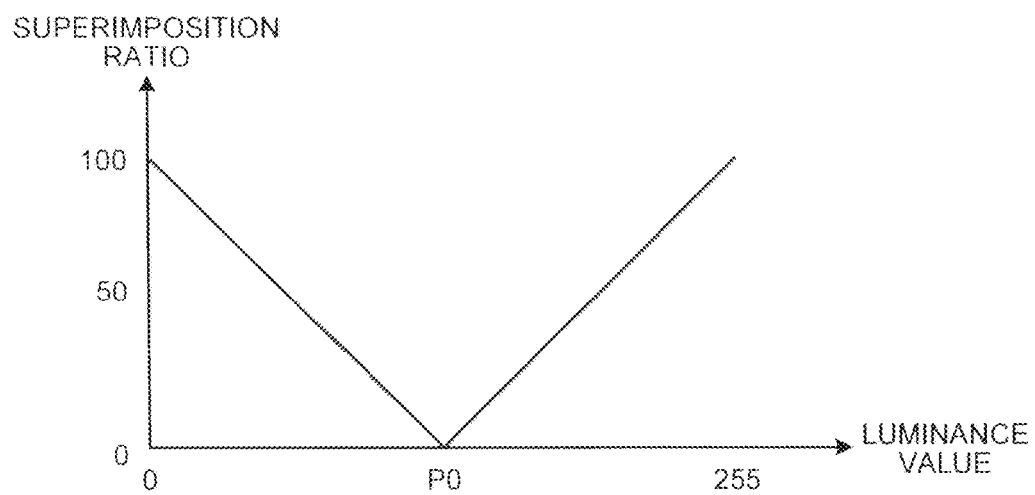
Figure 10:
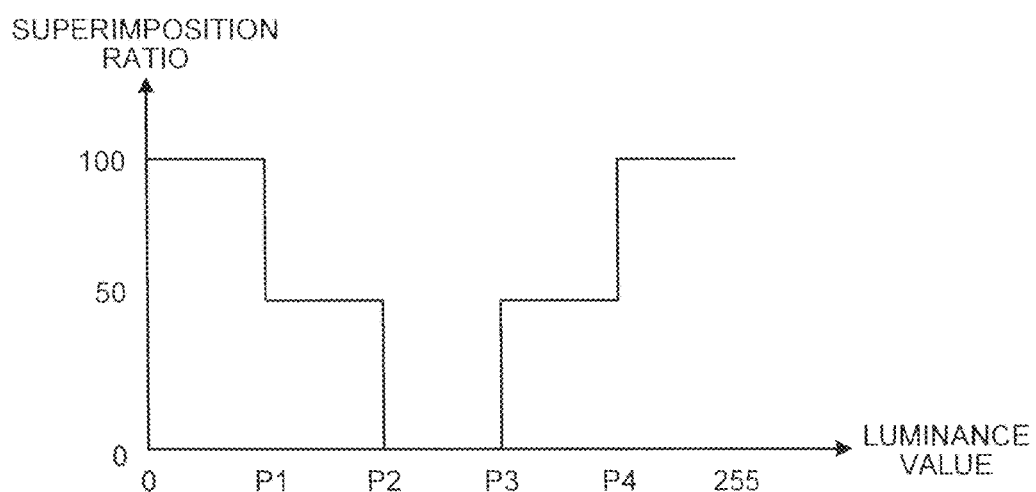

FIGS. 8 to 10 are explanatory diagrams of examples in which the superimposition processing unit sets a superimposition ratio. In FIGS. 8 to 10, the luminance value of the global illumination image is plotted on a horizontal axis and the superimposition ratio of the volume rendering image is plotted on a vertical axis. For example, the superimposition processing unit determines the superimposition ratio of the volume rendering image from a mean value of the luminance values of the global illumination image for each of the sections, based on the relation shown in FIGS. 8 to 10.

For example, as shown in FIG. 8, the relation between the luminance value of the global illumination image and the superimposition ratio of the volume rendering image is set so that as the luminance value of the global illumination image increases, the superimposition ratio of the volume rendering image decreases. Accordingly, in global illumination, in a dark section, the contour of the structure is more highlighted than in a bright area.

For example, as shown in FIG. 9, the relation between the luminance value of the global illumination image and the superimposition ratio of the volume rendering image is set such that the superimposition ratio is 100% with the luminance value being 0, the superimposition ratio is zero with the luminance value being P0, and the superimposition ratio is 100% with the luminance value being 255. Further, in the range of 0<luminance value<P0, it is set so that the superimposition ratio decreases as the luminance value increases, and in the range of P1<luminance value<255, it is set so that the superimposition ratio increases as the luminance value increases. Accordingly, in global illumination, the contour of the structure is more highlighted in the dark section and the bright section.

For example, as shown in FIG. 10, the relation between the luminance value of the global illumination image and the superimposition ratio of the volume rendering image is set such that the superimposition ratio is 100% with 0≤luminance value<P1, the superimposition ratio is 50% with P1≤luminance value<P2, the superimposition ratio is 0% with P2≤luminance value<P3, the superimposition ratio is 50% with P3≤luminance value<P4, and the superimposition ratio is 100% with P4≤luminance value =255. That is, in this case, the superimposition ratio of the volume rendering image is set stepwise with respect to the luminance value of the global illumination image.

The unit of division by the superimposition processing unit is not limited to the unit shown in FIG. 7, and division can be performed in a finer unit than the matrix of five rows and five columns, or in a coarser unit than the matrix of five rows and five columns. Further, the shape of the section is not limited to square and can be an arbitrary shape, for example, a rhombic or hexagonal shape. The size of the section does not need to be uniform, and for example, when distribution of the luminance is known beforehand, the section can be set finer for a range in which a change of the luminance is large, and the section can be set coarser for a range in which the change of the luminance is small.

For example, the superimposition processing unit can divide the superimposed image into pixels. In this case, for example, the superimposition processing unit determines the superimposition ratio of the volume rendering image from a mean value of the luminance value of the global illumination image, based on the relation between the luminance value of the global illumination image and the superimposition ratio of the volume rendering image shown in FIG. 8. In this manner, by dividing the superimposed image into pixels to set the superimposition ratio, a superimposed image in which a highlighting degree of the contour of the structure changes more naturally can be acquired, as compared to a case in which the superimposed image is divided into units larger than the pixel.

In the respective embodiments described above, there has been explained an example in which a global illumination image and a volume rendering image are superimposed on each other. However, the rendering method for generating rendering images to be superimposed on each other is not limited to a combination of global illumination and volume rendering.

That is, the ultrasonic diagnostic device includes a first rendering unit and a second rendering unit. The first rendering unit generates a first rendering image according to a first rendering method based on volume data collected by three-dimensionally scanning a subject with ultrasonic waves. The second rendering unit generates a second rendering image according to a second rendering method that is different from the first rendering method, based on the volume data.

For example, the first rendering method generates a shaded rendering image. In this case, for example, the second rendering method generates a rendering image having a less shaded area as compared to the first rendering method. That is, the second rendering method forms an image in which the contour of a structure is clearly drawn as compared to the first rendering method. By superimposing the rendering images generated by such a combination of rendering methods, a portion of the first rendering image generated by the first rendering method, in which the contour is unclear due to a shadow, can be supplemented by the second rendering image generated by the second rendering method.

For example, the first rendering method is global illumination or a gradient method. The second rendering method is, for example, volume rendering or surface rendering without any shading.

According to at least one of the above embodiments, an observation target can be easily observed on a rendering image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic device, comprising:
   an ultrasonic probe configured to collect volume data by three-dimensionally scanning a subject with ultrasonic waves; and
   processing circuitry configured to
      generate a first rendering image based on the volume data collected by the ultrasonic probe, by using a first rendering method, the first rendering method including rendering the volume data by global illumination;
      generate a second rendering image based on the volume data, by using a second rendering method that is different from the first rendering method;
      generate a superimposed image in which at least a part of the first rendering image and a part of the second rendering image are superimposed on each other;
      cause a display to display the superimposed image;
      determine whether the superimposed image is suitable for observation based on a luminance value of the superimposed image; and
      adjust so as to increase a superimposition ratio of the first rendering image or the second rendering image in the superimposed image, when it is determined that the superimposed image is not suitable for observation.

2. The ultrasonic diagnostic device according to claim 1, wherein the processing circuitry is further configured to generate a shaded rendering image as the first rendering image.

3. The ultrasonic diagnostic device according to claim 1, wherein the processing circuitry is further configured to adjust the superimposition ratio based on at least one of the first rendering image and the superimposed image.

4. The ultrasonic diagnostic device according to claim 1, wherein the processing circuitry is further configured to
receive an operation to change the superimposition ratio from an operator, and
adjust the superimposition ratio according to the received operation.

5. The ultrasonic diagnostic device according to claim 1, wherein the processing circuitry is further configured to superimpose the first rendering image and the second rendering image in a predetermined area of the superimposed image.

6. The ultrasonic diagnostic device according to claim 1, wherein the processing circuitry is further configured to divide the superimposed image into a plurality of sections, and set a superimposition ratio for each of the sections.

7. The ultrasonic diagnostic device according to claim 1, wherein the processing circuitry is further configured to determine whether the superimposed image is suitable for observation based on a mean value or a variance value of the luminance value of the superimposed image.

8. The ultrasonic diagnostic device according to claim 1, wherein
the processing circuitry is further configured to monitor a positional relation among an observing point used for rendering of the first rendering image and rendering of the second rendering image, a virtual light source used for rendering of the first rendering image, and a structure included in the volume data, and
when the virtual light source moves behind the structure, the processing circuitry is configured to determine that the superimposed image is not suitable for observation.

9. The ultrasonic diagnostic device according to claim 1, wherein the processing circuitry is further configured to generate the superimposed image by superimposing a two-dimensional image generated as a result of rendering of the first rendering image and a two-dimensional image generated as a result of rendering of the second rendering image on each other.

10. The ultrasonic diagnostic device according to claim 1, wherein the processing circuitry is further configured to generate the superimposed image by superimposing three-dimensional data generated before rendering of the first rendering image is performed and three-dimensional data generated before rendering of the second rendering image is performed on each other.

11. An image processing device, comprising:
processing circuitry configured to
acquire volume data collected by an ultrasonic probe configured to collect the volume data by three-dimensionally scanning a subject with ultrasonic waves;
generate a first rendering image based on the volume data by using a first rendering method, the first rendering method including rendering the volume data by global illumination;
generate a second rendering image based on the volume data by using a second rendering method that is different from the first rendering method;
generate a superimposed image in which at least a part of the first rendering image and a part of the second rendering image are superimposed on each other;
cause a display to display the superimposed image,
determine whether the superimposed image is suitable for observation based on a luminance value of the superimposed image, and
adjust so as to increase a superimposition ratio of the first rendering image or the second rendering image in the superimposed image, when it is determined that the superimposed image is not suitable for observation.

12. An image processing method, comprising:
acquiring volume data collected by an ultrasonic probe configured to collect volume data by three-dimensionally scanning a subject with ultrasonic waves;
generating a first rendering image based on the volume data by using a first rendering method, the first rendering method including rendering the volume data by global illumination;
generating a second rendering image based on the volume data by using a second rendering method that is different from the first rendering method;
generating a superimposed image in which at least a part of the first rendering image and a part of the second rendering image are superimposed on each other; and
causing a display to display the superimposed image,
determining whether the superimposed image is suitable for observation based on a luminance value of the superimposed image, and
adjusting so as to increase a superimposition ratio of the first rendering image or the second rendering image in the superimposed image when it is determined that the superimposed image is not suitable for observation.

* * * * *